US006951665B2

(12) United States Patent
Isoda

(10) Patent No.: US 6,951,665 B2
(45) Date of Patent: Oct. 4, 2005

(54) RADIO-CONDUCTIVE MATERIAL, METHOD OF MANUFACTURING THE SAME, SOLID SENSOR USING THE SAME, METHOD OF MANUFACTURING RADIO-CONDUCTIVE FILM, AND RADIATION IMAGE READ-OUT APPARATUS

(75) Inventor: Yuji Isoda, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 10/706,051

(22) Filed: Nov. 13, 2003

(65) Prior Publication Data

US 2005/0170074 A1 Aug. 4, 2005

Related U.S. Application Data

(62) Division of application No. 09/777,682, filed on Feb. 7, 2001, now Pat. No. 6,717,173.

(30) Foreign Application Priority Data

| | | | |
|---|---|---|---|
| Feb. 8, 2000 | (JP) | ............................. | 2000/030331 |
| Feb. 16, 2000 | (JP) | ............................. | 2000/038368 |
| Feb. 18, 2000 | (JP) | ............................. | 2000/041697 |
| Feb. 24, 2000 | (JP) | ............................. | 2000/047527 |

(51) Int. Cl.[7] .............................................. A61M 36/14

(52) U.S. Cl. ....................... 427/5; 427/369; 427/376.1; 427/376.6

(58) Field of Search ...................... 427/5, 376.1, 376.6, 427/385.5, 369, 370

(56) References Cited

U.S. PATENT DOCUMENTS

| | | | | |
|---|---|---|---|---|
| 4,176,275 A | | 11/1979 | Korn et al. | |
| 4,450,126 A | | 5/1984 | Kesting | |
| 4,535,468 A | | 8/1985 | Kempter | |
| 4,961,209 A | | 10/1990 | Rowlands et al. | |
| 5,268,569 A | | 12/1993 | Nelson et al. | |
| 5,354,982 A | | 10/1994 | Nelson et al. | |
| 5,556,716 A | * | 9/1996 | Herron et al. | .............. 428/688 |
| 5,925,890 A | | 7/1999 | Van Den Bogaert et al. | |

OTHER PUBLICATIONS

Research Disclosure, "Method and device for recording and transducing an electromagnetic energy pattern," Jun. 1983, pp. 229-231.

Medical Physics, "X-ray imaging using amorphous selenium: Photoinduced discharge (PID) readout for digital general radiography," vol. 22, No. 12, Dec. 1995, pp. 1983-1996.

* cited by examiner

*Primary Examiner*—Bret Chen
(74) *Attorney, Agent, or Firm*—Sughrue Mion, PLLC

(57) ABSTRACT

A radio-conductive material which exhibits conductivity upon exposure to radiations is formed of alcohol-soluble nylon and inorganic material having radiation absorbing power.

7 Claims, 13 Drawing Sheets

PRIOR ART

RADIO-CONDUCTIVE MATERIAL, METHOD OF MANUFACTURING THE SAME, SOLID SENSOR USING THE SAME, METHOD OF MANUFACTURING RADIO-CONDUCTIVE FILM, AND RADIATION IMAGE READ-OUT APPARATUS

This is a divisional of application Ser. No. 09/777,682 filed Feb. 7, 2001 now U.S. Pat. No. 6,717,173; the disclosure of which is incorporated herein by reference.

BACKGROUND OF THE INVENTION

1. Field of the Invention

This invention generally relates to a radio-conductive material which is a photoconductive material sensitive to radiations, a method of manufacturing such a radio-conductive material, a solid sensor which is provided with radio-conductive material layer on which image information can be recorded as a pattern of electrostatic charges (an electrostatic latent image) formed upon exposure to radiations, a method of manufacturing a film of such a radio-conductive material, and a radiation image read-out apparatus using such a solid sensor.

2. Description of the Related Art

In order to reduce irradiation dose to the patient's and/or to improve diagnostic performance of the radiation image in a medical radiography, there have been proposed various systems in which a photoconductive body sensitive to a radiation (e.g., a-Se (amorphous selenium) plate) is used as an electrostatic recording medium, and an electrostatic latent image formed on the photoconductive body upon exposure to a radiation is read out by a laser beam or a number of electrodes. For example, see U.S. Pat. Nos. 4,176,275, 5,268,569, 5,354,982, and 4,535,468, "23027 Method and Device for recording and transducing an electromagnetic energy pattern"; Research Disclosure June 1983, Japanese Unexamined Patent Publication No. 9(1997)-5906, U.S. Pat. No. 4,961,209, and "X-ray imaging using amorphous selenium"; Med Phys. 22 (12).

These systems are higher in resolution than known fluoroscopy using a TV pickup tube and less in irradiation dose to the patients than xeroradiography.

The radio-conductive material for forming the photoconductive body of the systems described above should be high in resistance in the dark, withstand a high electric field (e.g., $10^5$ to $10^6$ V $cm^{-1}$), be high in radiation absorbance and be able to establish a high electric charge. Further the radio-conductive material should be able to form a film so that electric charges can move in the film without being trapped.

However the selenium radio-conductive materials which have been generally used in the conventional systems are difficult to form a film thin enough to prevent electric charge trapping and are not satisfactory in radiation absorbance though they are excellent is durability and able to establish high electric charges. Further since selenium is designated as poison by law, it is preferred that the radio-conductive material does not contain selenium.

As substitute radio-conductive material for selenium, inorganic/organic composite material formed of organic material and $V_B$–$VI_B$, $V_B$–$VII_B$, $II_B$–$VI_B$, $II_B$–$V_B$, $III_B$–$V_B$, $III_B$–$VI_B$, $I_B$–$VI_B$ or $IV_B$–$VII_B$ inorganic material is disclosed in U.S. Pat. No. 5,556,716. For example, composite radio-conductive materials formed of inorganic material selected from the group consisting of $BiI_3$, $PbI_4$, $PbI_3$ and $Bi_2S_3$ and organic material selected from the group consisting of nylon 11, PVK (N-polyvinyl carbazole) and PMMA (polymethyl methacrylate) are disclosed in the patent.

That $BiI_3$/nylon 11 (50%/50% by weight) is a radio-conductive material which exhibits good radio-conductive-properties is described in "Science, 273(1966), 632".

The prior arts described above make it feasible to employ heavy element compounds, such as $BiI_3$ which have been said to be not suitable as radio-conductive material since they are difficult to form a high quality film in a large area, are large in dark current and accordingly are not able to withstand a high electric field though being excellent in radiation absorbance, as radio-conductive material by forming a composite of such heavy element compounds with organic material (high-molecular material) which is relatively easy to form a high quality thin film, is small in dark current and is excellent in dielectric properties.

However the inorganic/organic composite materials are disadvantageous in that dispersion of the inorganic material (inorganic fine particles) in the organic material is apt to be deteriorated. That is, since the inorganic/organic radio-conductive materials are generally manufactured by so-called "melt deposition process" in which organic material 81 is melted on a substrate 83 (FIG. 8) heated by a hot plate 82, inorganic particles are added to the molten organic material 81, and the mixture is stirred by, for instance, a spatula to form a film, it is difficult to uniformly disperse the inorganic particles in the organic material. When dispersion of the inorganic particles is not satisfactory, agglomerates of the inorganic particles are left in the formed thin film. The agglomerates deteriorate radio-conductive properties and durability to high electric fields, and can cause electric charge trapping.

Further, since, in the inorganic/organic composite materials, the radio-conductive inorganic material is "diluted" by the organic material, the inorganic material content should be high in order to ensure a satisfactory radiation absorbance. For example, in the case of $BiI_3$/nylon 11, the $BiI_3$ content should be not smaller than 65 wt % in order to obtain a radiation absorbance equivalent to the conventional radio-conductive material of selenium under normal diagnostic radiographic conditions. In known combinations of inorganic material and organic material, it is impossible to uniformly disperse the inorganic material in such a high content, and accordingly, the radio-conductive properties of the radio-conductive material obtained cannot be high.

Further, when a thin film such as a radio-conductive layer is formed of the inorganic/organic radio-conductive material, voids can be embedded in the film, which reduces the inorganic material content in the inorganic/organic radio-conductive material and further deteriorates the radio-conductive properties of the radio-conductive material. Further the voids can deteriorate transfer efficiency of electric charges formed upon exposure to radiations.

Further, since the inorganic/organic composite radio-conductive material is in the form of a nano-composite in which the inorganic material is in the form of fine particles of several nanometers to several tens of nanometers, fine unevenness exists on the surface of a solid sensor formed of the inorganic/organic composite radio-conductive material, and accordingly, an electrode formed on the surface of the solid sensor, for instance, deposition of Au cannot microscopically be in close contact with the radio-conductive layer. That is, gaps are microscopically formed between the electrode. Such gaps form charge wells in which electric charges formed in the radio-conductive layer concentrates, which can cause a stray current.

SUMMARY OF THE INVENTION

In view of the foregoing observations and description, the primary object of the present invention is to provide a radio-conductive material in which inorganic material is uniformly dispersed in organic material and which is good in radio-conductive properties and withstands a high electric field.

Another object of the present invention is to provide a method of manufacturing such a radio-conductive material.

Still another object of the present invention is to provide a solid sensor for recording a latent radiation image provided with a radio-conductive layer formed of a radio-conductive material which is good in radio-conductive properties, withstands a high electric field and is free from electric charge trapping.

Still another object of the present invention is to provide a method of manufacturing a radio-conductive film which is formed of inorganic/organic composite radio-conductive material and which is extremely small in void volume and accordingly large in inorganic material content.

Still another object of the present invention is to a provide solid sensor which is provided with a radio-conductive layer formed of inorganic/organic composite radio-conductive material and is free from a charge well which can cause a stray current.

That is, in accordance with a first aspect of the present invention, there is provided a radio-conductive material comprising alcohol-soluble nylon and inorganic material having radiation absorbing power.

In this specification, "radiation" means, for instance, X-rays, $\gamma$-rays and the like.

It is preferred that the inorganic material be bismuth iodide.

The alcohol-soluble nylon is a nylon which is solid at normal temperatures and is soluble in alcoholic solvent. For example, the alcohol-soluble nylon may be copolymer nylon obtained by copolymerizing various dibasic acids and diamines or nylon obtained by introducing an N-alkoxymethyl group into a polyamide binding of nylon. It is preferred that the alcohol-soluble nylon be composite material of nylon 6 and nylon 66.

It is further preferred that the radio-conductive material of the first aspect of the present invention be in the form of nano-composite.

In accordance with a second aspect of the present invention, there is provided a method of manufacturing radio-conductive material comprising the steps of dissolving alcohol-soluble nylon and inorganic material having radiation absorbing power in alcohol, and evaporating the alcohol to obtain high-viscosity composite material. This method will be referred to as "liquid deposition process", hereinbelow. The high-viscosity composite material thus obtained is formed into a film or the like.

In accordance with a third aspect of the present invention, there is provided a solid sensor characterized by having a radio-conductive layer formed of the radio-conductive material in accordance with the first aspect of the present invention.

In the radio-conductive material in accordance with the first aspect of the present invention, since alcohol-soluble nylon is employed as the organic material and the organic material can be dissolved in alcohol, which facilitates to uniformly dispersing the inorganic material. Accordingly, the radio-conductive material can be a radio-conductive material which has both advantages of inorganic material, i.e., it is excellent in radiation absorbance, and advantages of organic material, i.e., it can be formed into a high quality film. Since being free from agglomerates of the inorganic particles, a film (e.g., a radio-conductive layer) formed of the radio-conductive material of the first aspect of the present invention can be better in radio-conductive properties, is less apt to cause electric charge trapping, and can be small in dark current which flows while the film is not being exposed to radiations.

Further, since the inorganic material can be uniformly dispersed in the organic material even if the organic material content is high, the radio-conductive properties of the film can be more improved.

Further, in accordance with the method of manufacturing the radio-conductive material of the third aspect, handling properties are improved and stability of the radio-conductive material manufactured can be highly improved.

In accordance with a fourth aspect of the present invention, there is provided a radio-conductive material represented by the following formula (I), $$BiI_3/x.MX/y.\text{nylon} \qquad (I),$$

wherein M represents at least one alkali metal selected from the group consisting of Li, Na, K, Rb and Cs, X represents at least one halogen selected from the group consisting of F, CI, Br and I, and x and y respectively represent the ratios by weight of MX and nylon to $BiI_3$, x being $0<x<1$, and y being $0<y<4$.

It is preferred that MX be potassium fluoride.

It is further preferred that the radio-conductive material of the fourth aspect of present invention be in the form of nano-composite.

It is preferred that the nylon be alcohol-soluble. The alcohol-soluble nylon is a nylon which is solid at normal temperatures and is soluble in alcoholic solvent. For example, the alcohol-soluble nylon may be copolymer nylon obtained by copolymerizing various dibasic acids and diamines or nylon obtained by introducing an N-alkoxymethyl group into a polyamide binding of nylon. It is preferred that the alcohol-soluble nylon be composite material of nylon 6 and nylon 66.

It is preferred that the alkali halide represented by MX be alcohol-soluble.

Preferably $0<x<0.2$ and $0.1<y<1$.

In accordance with a fifth aspect of the present invention, there is provided a solid sensor characterized by having a radio-conductive layer formed of the radio-conductive material in accordance with the fourth aspect of the present invention.

In the radio conductive material in accordance with the fourth aspect of the present invention, the alkali halide (MX) adheres to the surface of the bismuth iodide and changes the surface profile of the bismuth iodide, whereby the ratio of the bismuth iodide content to the nylon content can be increased. This means that the radiation absorbance of the radio-conductive material can be increased since the component of the radio-conductive material having radiation absorbing power is bismuth iodide.

Further, since the alkali halide changes the surface profile of the bismuth iodide, the radio-conductive material can be easily formed into a film even if the bismuth iodide content is high. Further, since dispersion of bismuth iodide is good, the radio-conductive layer of a solid sensor formed of the radio-conductive material of the fourth aspect of the present invention satisfactorily withstands a high electric field and is less in charge trapping.

Though the thin film of radio-conductive material is generally saturated with charges as the voltage applied to the film is increased, the film of the radio-conductive material in accordance with the fourth aspect of the present invention is hard to saturate with charges. It may be conceived that this is because there is no place where electric charges are gathered such as agglomerates of the inorganic particles in the formed thin film, and because the surface profile of the radio-conductive layer is changed. When the film is not saturated with electric charges with increase in the applied voltage, the radio-conductive properties of the solid sensor can be improved.

In accordance with a sixth aspect of the present invention, there is provided a method of manufacturing a radio-conductive film of an inorganic/organic composite radio-conductive material comprising the step of pressing the inorganic/organic composite radio-conductive material.

The radio-conductive material before pressing may be in the form of a block or in the form a film.

It is preferred that the inorganic/organic composite radio-conductive material be pressed at an elevated temperature. Preferably the elevated temperature be in the range of 50° C. to 200° C., and more preferably 120° C. to 190° C.

It is preferred that the inorganic/organic composite radio-conductive material be pressed at not higher than 50 $Kg/cm^2$.

In accordance with a seventh aspect of the present invention, there is provided a method of manufacturing a radio-conductive film of an inorganic/organic composite radio-conductive material comprising the step of heating a film of inorganic/organic composite radio-conductive material.

It is preferred that the inorganic/organic composite radio-conductive material be $BiI_3$/nylon.

In accordance with the methods of manufacturing a radio-conductive film of the sixth and seventh aspects of the present invention, the radio-conductive film formed can be extremely small in void volume and accordingly can be better in radio-conductivity.

In accordance with an eighth aspect of the present invention, there is provided a solid sensor comprising a radio-conductive layer formed of inorganic/organic composite material and an electrode provided on the radio-conductive layer, wherein the improvement comprises that the electrode is of indium.

In accordance with a ninth aspect of the present invention, there is provided a radiation image read-out apparatus comprising a solid sensor in accordance with the eighth aspect of the present invention and a read-out means for reading out a radiation image recorded on the solid sensor as a latent radiation image.

Indium is the softest in metals which are solid and stable at normal temperatures, is superior in processing characteristics, and can be almost freely deformed. Accordingly, the indium electrode can be in close contact with the radio-conductive layer formed of inorganic/organic composite material without any gap formed therebetween, whereby no charge well is formed in the solid sensor and the radio-conductivity of the solid sensor can be improved.

DETAILED DESCRIPTION OF THE INVENTION

Figure 1:
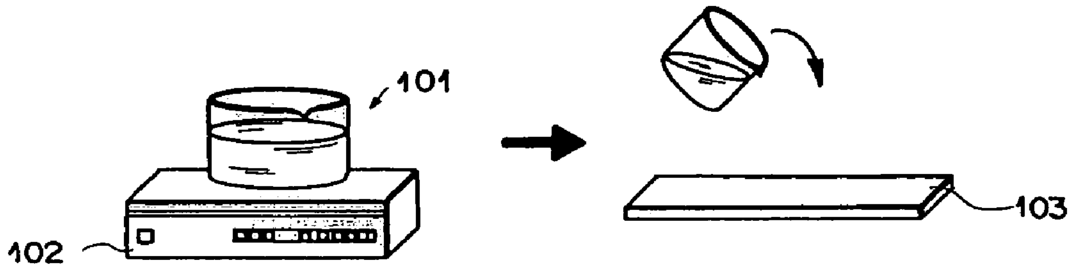
FIG. 1 is a schematic view showing process of manufacturing radio-conductive material of the present invention.

The radio-conductive material, the method and the solid sensor in accordance with the first to third aspects of the present invention will be described in more detail.

The radio-conductive material in accordance with the first aspect of the present invention comprises alcohol-soluble nylon and inorganic material having radiation absorbing power.

The inorganic material having radiation absorbing power may be $V_B$–$VI_B$, $V_B$–$VII_B$, $II_B$–$VI_B$, $II_B$–$V_B$, $III_B$–$V_B$, $III_B$–$VI_B$, $I_B$–$VI_B$ or $IV_B$–$VII_B$ inorganic material. For example, the inorganic material may be $Bi_2S_3$, $Bi_2Se_3$, $BiI_3$, $BiBr_3$, CdS, CdSe, CdTe, HgS, $Cd_2P_3$, InAs, InP, $In_2S_3$, $In_2Se_3$, $Ag_2S$, $PbI_2$ or $PbI_4^{2-}$. Among those, $BiI_3$ (bismuth iodide) is especially preferred.

The alcohol-soluble nylon is a nylon which is solid at normal temperatures and is soluble in alcoholic solvent. For example, the alcohol-soluble nylon may be copolymer nylon obtained by copolymerizing various dibasic acids and diamines or nylon obtained by introducing a N-alkoxymethyl group into a polyamide binding of nylon as described above.

The copolymer nylon is obtained by copolymerizing two or more dibasic acids and/or two or more diamines. As the diamine, hexamethylenediamine, heptamethylenediamine, p-diaminomethylcyclohexane, bis-(p-aminocyclohexyl) methane, m-xylenediamine, 1,4-bis(3-aminopropoxy)cyclohexane, piperazine, isophoronediamine and the like may be used. As the dibasic acid, adipic acid, sebacic acid, azelaic acid, dodecanoic acid, undecanoic acid, dimmer acid, phthalic acid, isophthalic acid, terephthalic acid, sodium 5-sulfoisophthalate, and the like may be used. Further the alcohol-soluble nylon may be produced from aminocarboxylic acids such as 11-aminoundecanoic acid, 12-aminododecanoic acid, 4-aminomethylbenzoic acid, 4-aminomethylcyclohexanecarboxylic acid, 7-aminoenanthic acid, and 9-aminononanoic acid, and lactams such as ϵ-caprolactam, ω-laurolactam, α-pyrrolidone, and α-piperidone. The alcohol-soluble nylons obtained from these compounds include nylon 6/nylon 66, nylon 6/nylon 6–10, nylon 6/nylon 66/nylon 6–10, nylon 6/nylon 66/nylon 11, nylon 6/nylon 66/nylon 12, nylon 6/nylon 6–10/nylon 6–11, nylon 6/nylon 6–10/nylon 6–12, nylon 6/nylon 11/isophoronediamine, nylon 6/nylon 66/p-di(aminocyclohexyl)methane and the like. Among those, composite material of nylon 6 and nylon 66 is especially preferred.

The alcohol-soluble nylon may be obtained by introducing an N-alkoxymethyl group in to a polyamide binding of nylon. For example, nylon obtained by alkoxymethylation of nylon 6 or nylon 66 may be used. Introduction of an N-alkoxymethyl group contributes to lowering the melting point, increasing flexibility and improving dissolution.

Such alcohol-soluble nylons are wide known and may be manufactured according to the process disclosed in, for instance, "Nylon Resin Handbook", and "Journal of American Chemical Society" (71, 651, 1949).

The alcohol-soluble nylon/inorganic material ratio depends upon the alcohol-soluble nylon and the inorganic material used. For example, when the alcohol-soluble nylon is nylon 6/nylon 66 composite material and the inorganic material is bismuth iodide, the nylon/$BiI_3$ ratio is preferably 50–10/50–90% by weight, and more preferably 35–15/65–85% by weight.

The alcohol in which bismuth iodide and nylon 6/nylon 66 composite material are dissolved may be methanol, ethanol, isopropyl alcohol, n-propyl alcohol, isobutyl alcohol, n-butyl alcohol and the like. In order to evaporate the alcohol after dissolving the nylon and the inorganic material in the alcohol to obtain high-viscosity composite material, methanol and ethanol are preferred. It is preferred that the alcohol be dehydrated, for instance, by a molecular sieve. Though depending upon the kinds of alcohol to be used, the nylon/inorganic material ratio of the mixture to be dissolved in the alcohol, and the like, it is preferred that the alcohol be used in an amount sufficient for the nylon to be dissolved in the alcohol and for the inorganic material to be satisfactorily dispersed in the alcohol.

The radio-conductive material in accordance with the first aspect of the present invention may be manufactured by the "liquid deposition process". The manufacture of the radio-conductive material in accordance with the first aspect of the present invention by the "liquid deposition process" will be described in detail with reference to FIG. 1 taking as example the case where the inorganic material is bismuth iodide and the alcohol-soluble nylon is nylon 6/nylon 66 composite material. Bismuth iodide and nylon 6/nylon 66 composite material (in the ratio of 65–50/35–50% by weight) are introduced into alcohol in a beaker 101 and the mixture is heated to a predetermined temperature by a heating apparatus (e.g., a hot plate) 102 while stirring the mixture as shown in FIG. 1 so that the bismuth iodide and the nylon are satisfactorily dissolved in the alcohol. Though depending upon the kind of the alcohol, the predetermined temperature is preferably in the range of a room temperature (about 25° C.) to 60° C. The ratio of the bismuth iodide to the nylon to the alcohol is, for instance, 1 g: 1 g: 100 ml. Then the mixture is heated at 60° C. while stirring the mixture, thereby further evaporating the alcohol to obtain high-viscosity bismuth iodide/nylon 6/nylon 66 composite material. Then the high-viscosity composite material is dropped onto a substrate 103 of aluminum, ITO or the like and is formed into a film by the use of a spatula or the like. Thereafter the substrate 103 bearing thereon the film of bismuth iodide/nylon 6/nylon 66 composite material is left in methanol and is gradually dried. If desired other materials such as additives may be added for various purposes.

Latent radiation image recording and latent radiation image reading using a solid sensor having a radio-conductive layer formed of a radio-conductive material in accordance with the first aspect of the present invention will be described with reference to FIGS. 2 to 5D, hereinbelow.

Figure 2:
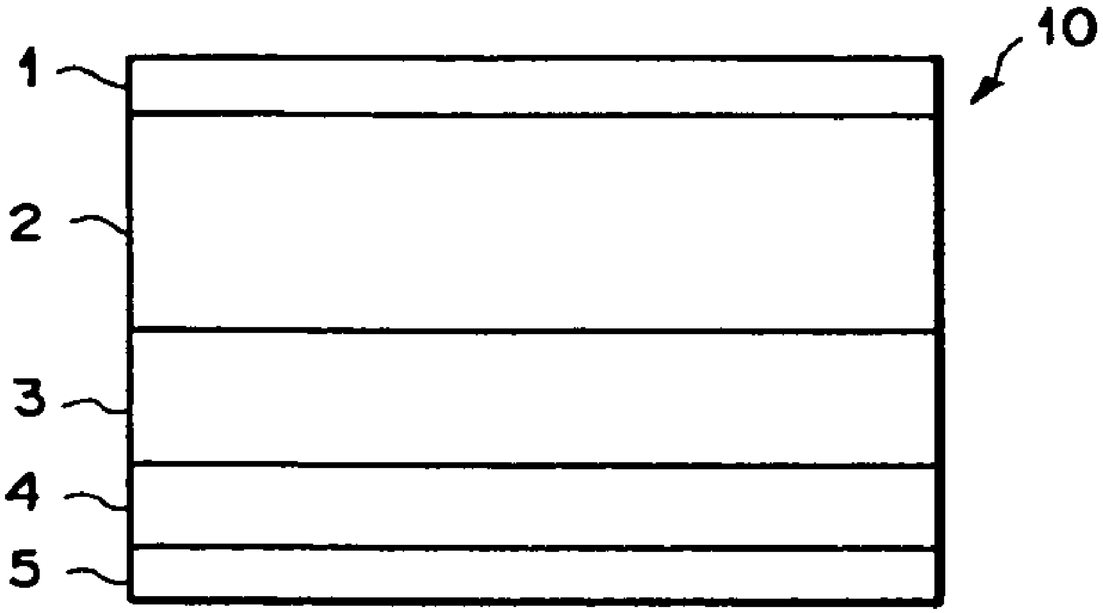
FIG. 2 is a cross-sectional view showing a solid sensor in accordance with an embodiment of the present invention.

FIG. 2 shows a solid sensor having a radio-conductive layer formed of a radio-conductive material in accordance with the first aspect of the present invention. The solid sensor 10 comprises a first conductive layer 1 which is permeable to a recording radiation L1 to be described later, a recording radio-conductive layer 2 which becomes conductive when exposed to the recording radiation L1 passing through the first conductive layer 1, a charge transfer layer 3 which acts as an insulating layer to the electric charge of the polarity at which the first conductive layer 1 is electrified (latent image polarity: e.g., negative polarity) while acts as a conductive layer to the electric charge of the polarity opposite to the latent image polarity (transfer polarity: e.g., positive polarity), a read-out photoconductive layer 4 which becomes conductive when exposed to read-out light L2, and a second conductive layer 5 which is permeable to the read-out light L2, the layers 1 to 5 being superposed one on another in this order.

As the first and second conductive layers 1 and 5, those obtained by uniformly coating conductive material on a glass plate (a so-called nesa-film) are suitably used. As the charge transfer layer 3, those in which the difference in mobility between negative and positive charges is larger (e.g., not smaller than $10^2$, and preferably not smaller than $10^3$) is better, and organic compounds such as PVK (N-polyvinyl carbazole), N,N'-diphenyl-N,N'-bis(3-methylphenyl)-[1,1'-biphenyl]-4,4'-diamine (TPD), and a discotheque liquid crystal; dispersion of TPD in polymer (polycarbonate, polystyrene, PUK or the like); or semiconductors such as a-Se doped with 10 to 200 ppm of Cl are suitable. Especially, organic compounds such as PVK, TPD and discotheque liquid crystals are preferred because of their insensitivity to light. Further, since those organic compounds are generally small in dielectric constant, which makes smaller the capacities of the charge transfer layer 3 and the read-out photoconductive layer 4 and increases the signal fetch efficiency upon read-out.

The read-out photoconductive layer 4 may be suitably formed of photoconductive material which includes as its major component at least one of a-Se, Se—Te, Se—As—Te, metal-free phthalocyanine, metallophthalocyanine, MgPC (magnesium phthalocyanine), VoPc (phase II of vanadyl phthalocyanine) and CuPc (copper phthalocyanine).

It is preferred that the charge transfer layer 3 and the photoconductive layer 4 be not larger than ½ of the thickness of the recording radio-conductive layer 2, and the thinner the charge transfer layer 3 and the photoconductive layer 4 are (e.g., not thicker than 1/10 or 1/20 of the recording radio-conductive layer 2), the higher the read-out response of the solid sensor is.

The recording radio-conductive layer 2 is formed of radio-conductive material in accordance with the first aspect of the present invention. Preferably the thickness of the recording radio-conductive layer 2 is in the range of 100 μm to 2000 μm and more preferably in the range of 500 μm to 1000 μm so that the recording radio-conductive layer 2 can sufficiently absorb the recording radiation L1.

A latent radiation image recorded on the solid sensor may be read out by a system which uses light, a system which uses transistors for respective pixels, and the like.

The system which uses light will be briefly described first.

Figure 3:
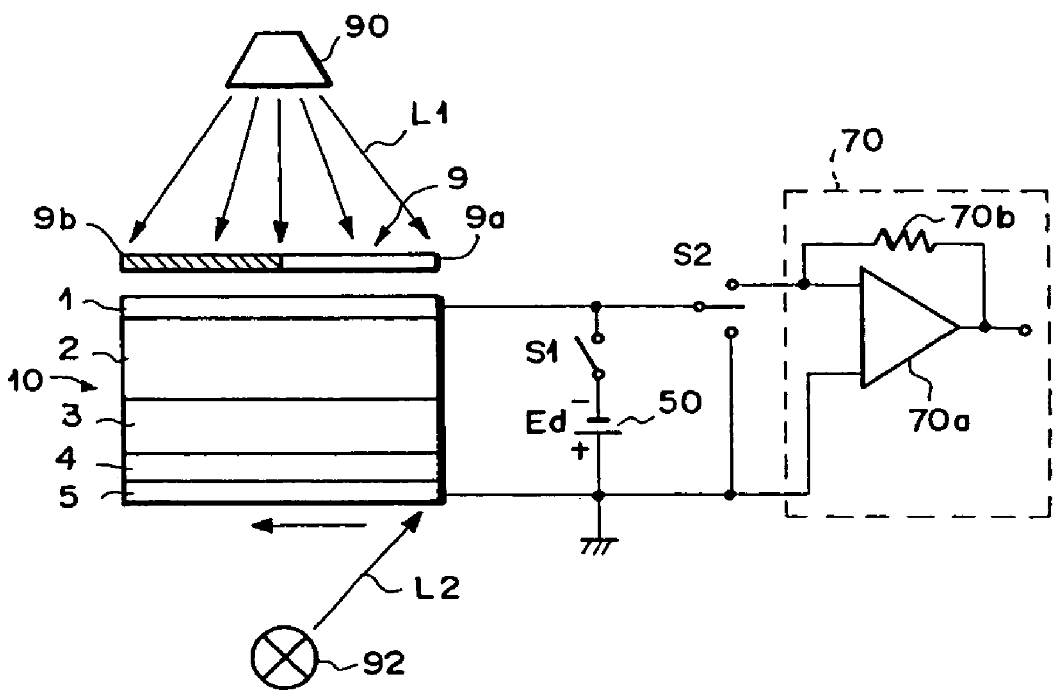
FIG. 3 is a schematic view showing a radiation image recording and read-out apparatus using the solid sensor of the embodiment.

FIG. 3 shows a radiation image recording and read-out apparatus using the solid sensor 10 of this embodiment. The radiation image recording and read-out apparatus comprises a solid sensor 10, a recording radiation projecting means 90, a power source 50, an electric current detecting means 70, a read-out light projecting means 92 and a pair of switching means S1 and S2. The solid sensor 10, the power source 50, the recording radiation projecting means 90 and the first switching means S1 form a latent radiation image recording system and the solid sensor 10, the electric current detecting means 70, the read-out light projecting means 92 and the second switching means S2 form a latent radiation image read-out system.

The first conductive layer 1 of the solid sensor 10 is connected to the negative pole of the power source 50 through the first switching means S1 and to a movable contact of the second switching means S2. The second switching means S2 has a pair of fixed contacts, one of which (a first fixed contact) is connected to the electric current detecting means 70 and the other of which (a second fixed contact) is grounded. The second conductive layer 5 of the solid sensor 10 and the positive pole of the power source 50 are grounded. The electric current detecting means comprises a detection amplifier 70*a* in the form of an operational amplifier and a feedback resistor 70*b* and forms a so-called current/voltage conversion circuit.

An object 9 is placed on the upper surface of the first conductive layer 1 of the solid sensor 10. The object 9 comprises a permeable part 9*a* which is permeable to the recording radiation L1 and an impermeable part 9*b* which is impermeable to the recording radiation L1. The object 9 is uniformly exposed to the recording radiation L1 by the recording radiation projecting means 90. The read-out light projecting means 92 causes the read-out light L2 to scan the solid sensor 10 in the direction of the arrow in FIG. 3. The read-out light L2 may be of infrared laser light, and is preferably converged into a beam of small diameter.

Figure 4A:
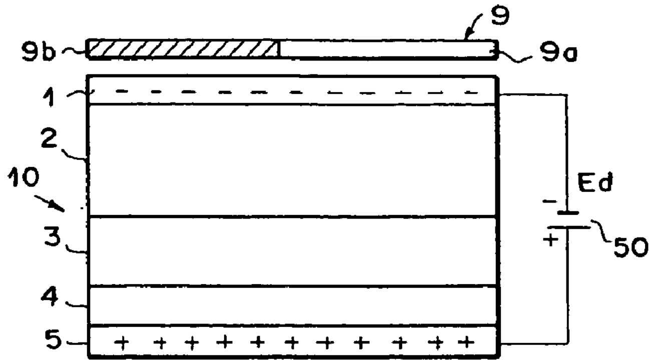
FIGS. 4A to 4D are views for illustrating latent radiation image recording process in the radiation image recording and read-out apparatus shown in FIG. 3, FIGS. 5A to 5D are views for illustrating latent radiation image read-out process in the radiation image recording and read-out apparatus shown in FIG. 3.

The latent radiation image recording process in the radiation image recording and read-out apparatus shown in FIG. 3 will be described with reference to the charge model shown in FIGS. 4A to 4D, hereinbelow. When a direct voltage Ed is applied between the first and second conductive layers 1 and 5 from the power source 50 by closing the first switching means S1 with the second switching means S2 kept open, i.e., with the movable contact kept away from both the first and second fixed contacts, the first conductive layer 1 is negatively charged and the second conductive layer 5 is positively charged as shown in FIG. 4A, whereby a parallel electric field is established between the first and second conductive layers 1 and 5 in the solid sensor 10.

Figure 4B:
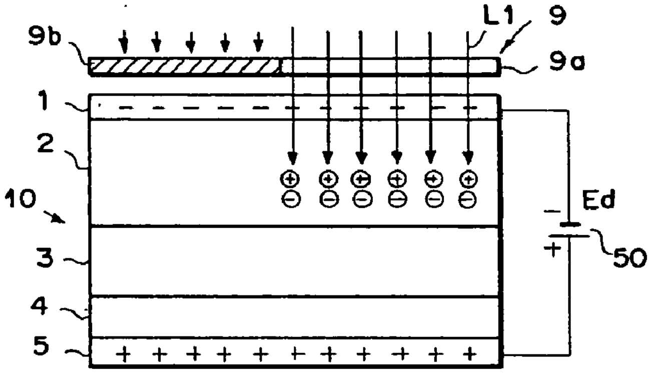
Figure 4C:
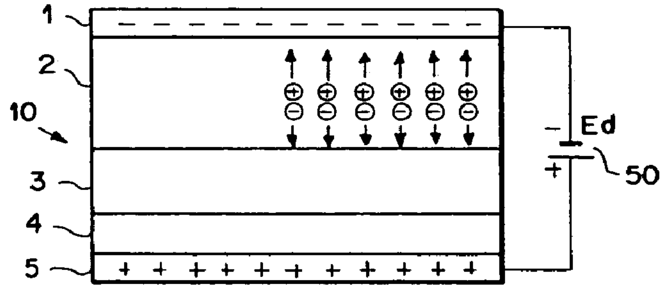
Figure 4D:
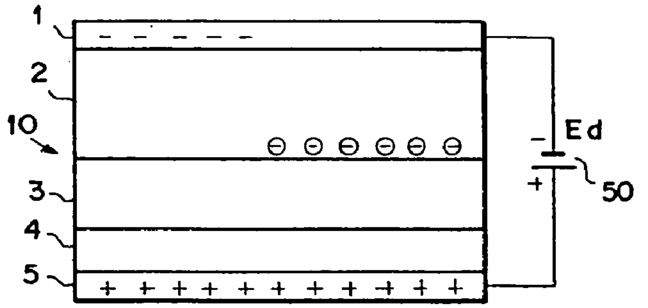

Thereafter the object 9 is uniformly exposed to the recording radiation L1 from the recording radiation projecting means 90. The part of the recording radiation L1 passing through the permeable part 9*a* of the object 9 impinges upon the radio-conductive layer 2 through the first conductive layer 1. The part of the radio-conductive layer 2 exposed to the recording radiation L1 becomes conductive. That is, each of parts of the radio-conductive layer 2 exposed to the recording radiation L1 behaves like a variable resistor whose resistance changes according to the amount of the recording radiation L1 to which the part is exposed. The resistance of each variable resistor depends upon electrons (a negative charge) and holes (a positive charge) generated upon exposure to the recording radiation L1, and as the amount of the recording radiation L1 passing through the object 9 to impinge upon the radio-conductive layer 2 becomes smaller, the resistance increases. (FIG. 4B)

The positive charge generated in the radio-conductive layer 2 moves toward the first conductive layer 1 at high speed and encounters the negative charge of the first conductive layer at the interface of the radio-conductive layer 2 and the first conductive layer 1 to cancel each other by recombination. The negative charge generated in the radio-conductive layer 2 moves toward the charge transfer layer 3 and is gathered at the interface of the radio-conductive layer 2 and the charge transfer layer 3. (FIGS. 4C and 4D) The amount of charge gathered at the interface depends upon the amount of the negative charge generated in the radio-conductive layer 2 upon exposure to the recording radiation L1, that is, the amount of the recording radiation passing through the object 9.

To the contrast, the part of the radio-conductive layer 2 behind the impermeable part 9*b* of the object 9 is kept unchanged since the part is not exposed to the recording radiation L1. (See FIGS. 4B to 4D) Thus, an electric charge is gathered on the interface of the radio-conductive layer 2 and the charge transfer layer 3 in a pattern corresponding to a radiation image of the object 9, that is, a latent radiation image is recorded.

The latent radiation image read-out process in the radiation image recording and read-out apparatus shown in FIG. 3 will be described with reference to the charge model shown in FIGS. 5A to 5D, hereinbelow.

The first switching means S1 is first opened to stop power supply to the solid sensor 10 from the power source 50 and the movable contact of the second switching means S2 is connected to the second fixed contact connected to the ground so that the first and second conductive layers 1 and 5 charged at the same potential. (FIG. 5A) After thus rearranging the charge, the movable contact of the second switching means S2 is connected to the first fixed contact connected to the electric current detecting means 70.

Figure 5A:
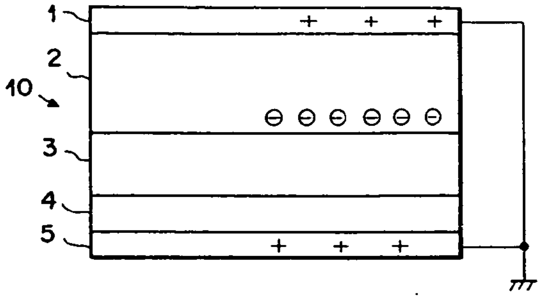
Figure 5B:
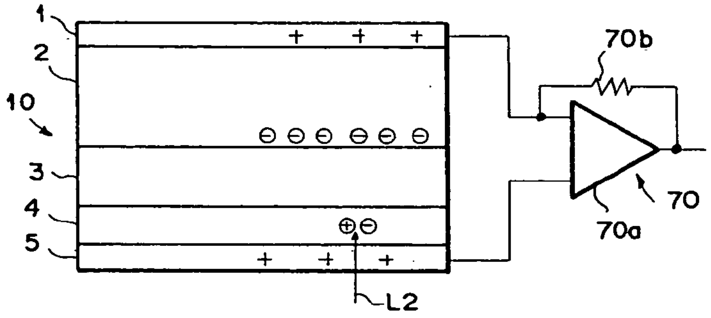
Figure 5C:
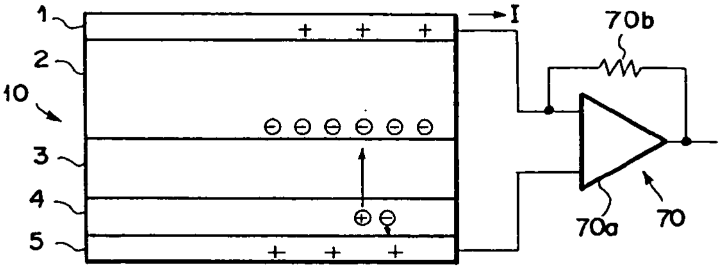

Then, when the read-out light projecting means 92 causes the read-out light L2 to scan the second conductive layer 5, the read-out light L2 impinges upon the photoconductive layer 4 through the second conductive layer 5. The part of the photoconductive layer 4 exposed to the read-out light L2 becomes conductive. (FIG. 5B)

Figure 5D:
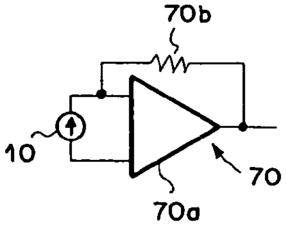

Since the charge transfer layer 3 is conductive to the positive charge, the positive charge generated in the photoconductive layer 4 moves toward the radio-conductive layer 2 at high speed attracted by the negative charge on the interface of the radio-conductive layer 2 and the charge transfer layer 3 and encounters the negative charge to cancel each other by recombination. The negative charge generated in the photoconductive layer 4 encounters the positive charge of the second conductive layer 5 and cancels each other by recombination. (FIG. 5C) The photoconductive layer 4 is exposed to a sufficient amount of read-out light L2, the whole charge gathered at the interface of the radio-conductive layer 2 and the charge transfer layer 3 is canceled by charge recombination. That the charged gathered by the solid sensor 10 is canceled means that the electric charge moves and an electric current I flows as shown in FIG. 5D as an equivalent circuit.

By thus detecting the electric current flowing out from the solid sensor 10 while scanning the solid sensor 10 with read-out light L2, the amounts of charges gathered at respective parts (corresponding to pixels) of the solid sensor 10 can be read out in sequence, whereby the latent radiation image can be read-out.

The radio-conductive material in accordance with the first aspect of the present invention can be also applied to a solid sensor in which a latent image is read out by TFT transistors. Such a solid sensor will be described with reference to FIGS. 6 and 7, hereinbelow.

Figure 6:
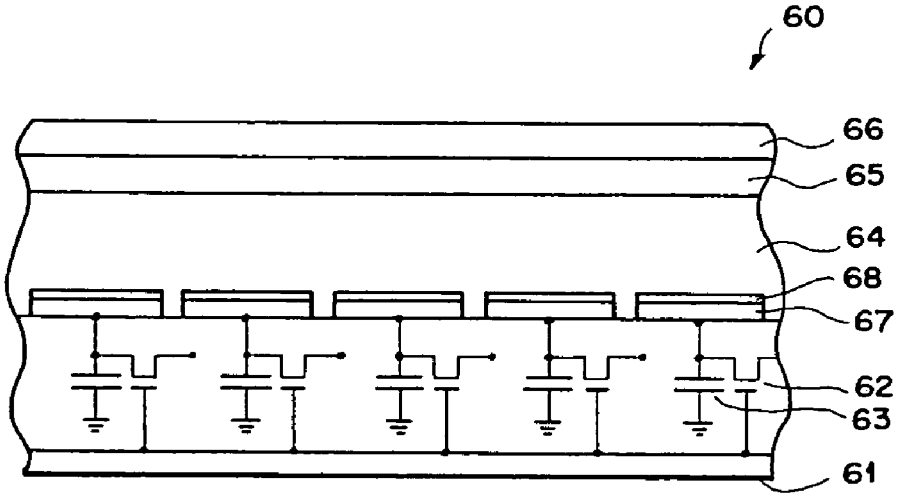
FIG. 6 is a cross-sectional view showing a solid sensor in accordance with another embodiment of the present invention.
Figure 7:
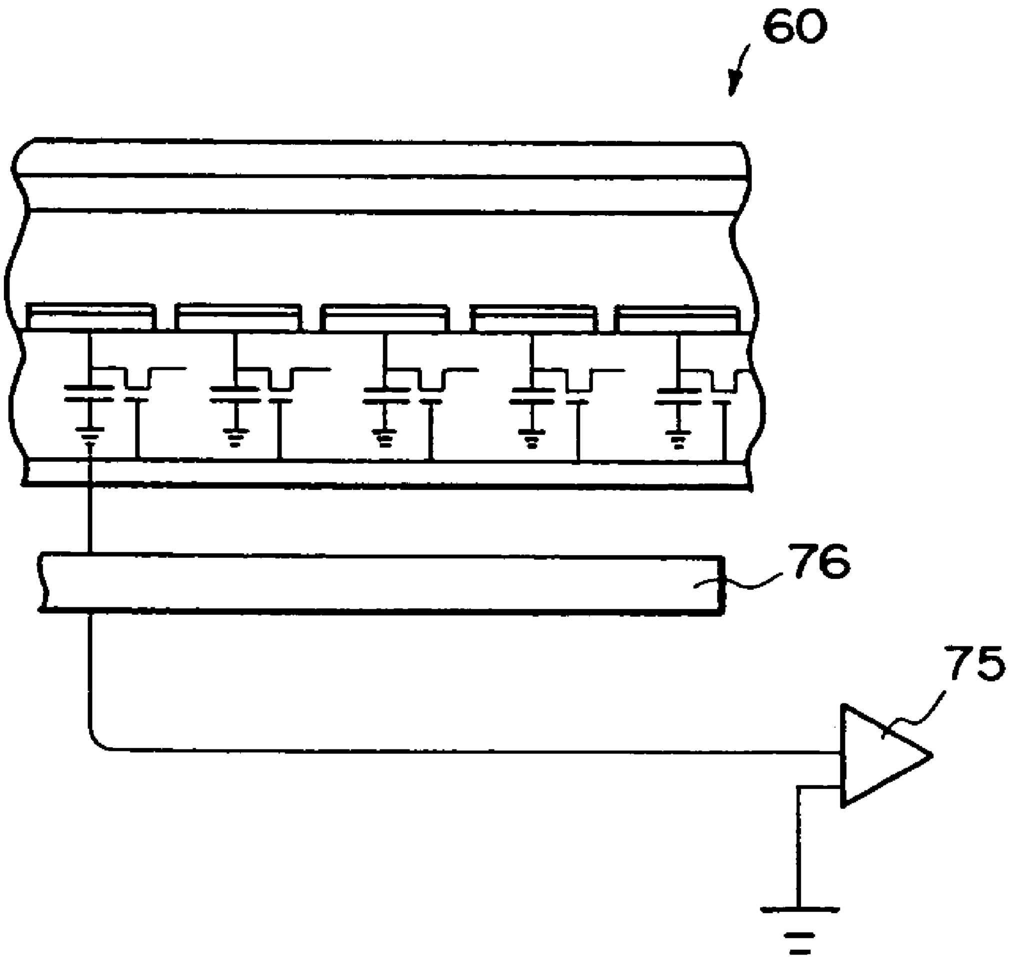
FIG. 7 is a schematic view showing a radiation image recording and read-out apparatus using the solid sensor shown in FIG. 6.
Figure 8:
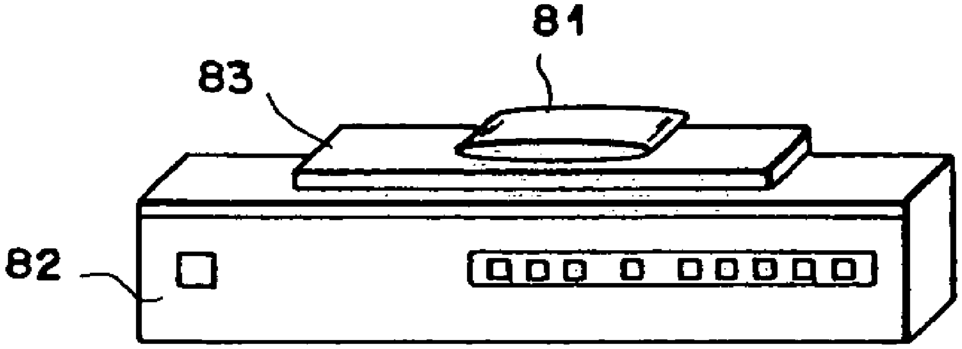
FIG. 8 is a schematic view showing conventional process of manufacturing radio-conductive material.

In FIGS. 6 and 7, a solid sensor 60 in accordance with a second embodiment of the present invention comprises a dielectric base 61, an array of a plurality of transistors 62 formed on the base 61, an array of a plurality of capacitors 63 formed on the base 61, a radio-conductive layer 64 formed over the transistors 62 and the capacitors 63, a barrier dielectric layer 65 formed over the radio-conductive layer 64 and an upper electrode 66 formed over the barrier dielectric layer 65. Each of the capacitors 63 is provided with a conductive inner micro plate 67 connected to the transistor 62, and a charge barrier layer 68 is formed on the surface of the inner micro plate 67. The radio-conductive layer 64 may be formed of the radio-conductive material in accordance with the first aspect of the present invention.

Latent radiation image recorded on the solid sensor 60 can be read out by taking out in time series an electric charge flowing out from the solid sensor 60 by a multiplexer 76 and detects the electric charge in sequence by a detector 75. See, for instance, "SPIE" vol. 2432/237.

A film of X-ray-conductive material in accordance with the first aspect of the present invention (embodiment 1) was produced together with films of X-ray-conductive material not in accordance with the first aspect of the present invention (comparative examples 1 and 2) in the following manner.

EMBODIMENT 1

1 g of bismuth iodide and 1 g of nylon CM4000 (available from Toray: nylon 6/nylon 66 composite material) were introduced into 100 ml of methanol which had been dehydrated by a molecular sieve, and the mixture was stirred at 60° C. so that the bismuth iodide and the nylon were satisfactorily dissolved in the methanol. Then the mixture was heated at 60° C. while stirring the mixture, thereby further evaporating the methanol to obtain high-viscosity bismuth iodide/nylon CM4000 composite material. Then the high-viscosity composite material was dropped onto an aluminum substrate (at 0 to 50° C.) and was formed into a film by the use of a spatula at the room temperature. Thereafter the substrate bearing thereon the film of bismuth iodide/nylon CM 4000 composite material was left in methanol and gradually dried. The film obtained exhibited X-ray-conductivity and was 200 $\mu$m in thickness.

COMPARATIVE EXAMPLE 1

Bismuth iodide and nylon CM4000 (available from Toray: nylon 6/nylon 66 composite material) were weighed in the ratio of 50/50% by weight. The nylon CM4000 was melted on an aluminum substrate at 180 to 210° C., and the weighed bismuth iodide was added to the molten nylon CM4000. The mixture was stirred and formed into a film by a spatula. Then the film was cooled to the room temperature. The film obtained exhibited X-ray-conductivity and was 200 $\mu$m in thickness.

COMPARATIVE EXAMPLE 2

An X-ray-conductive film 200 $\mu$m thick was obtained in the same manner as the comparative example 1 except that nylon 11 was employed in place of nylon CM4000.

Evaluation

The density of bismuth iodide and the photocurrent upon exposure to an X-ray of the X-ray-conductive films of the embodiment 1 and the comparative examples 1 and 2 were measured. The photocurrent was measured as a photocurrent per unit volume by sputtering gold in a size of 5 mm×5 mm×600 Å on the X-ray-conductive films and by the use of a D1 photoconductivity evaluation apparatus (X-ray: 80 kV-10~100 mR, detection: pico-ammeter) and a D6 photoconductivity evaluation apparatus (X-ray: 80, 120 kV-20 mR, detection: digital oscilloscope). The dark current was measured at a voltage at which the photocurrent is maximized. The result is shown in the following table.

TABLE 1

| | nylon | process | density ($g/cm^3$) | photocurrent ($A/cm^3$) | dark current ($\Omega \cdot cm$) |
|---|---|---|---|---|---|
| emb. 1 | nylon CM4000 | liquid deposition | 2.00 | $4.53 \times 10^{-8}$ | $2.5 \times 10^{-13}$ |
| comp. EX. 1 | nylon CM4000 | melt deposition | 2.02 | $3.36 \times 10^{-8}$ | — |
| comp. EX. 2 | nylon 11 | melt deposition | 1.28 | $7.56 \times 10^{-9}$ | $1.0 \times 10^{-19}$ |

As can be understood from table 1, in the embodiment 1, where alcohol-soluble nylon CM4000 (nylon 6/nylon 66 composite material) was employed, the density of the bismuth iodide was higher than in the comparative example 2, where alcohol-insoluble nylon 11 was employed, and the photocurrent was 4.4 times (2.8 times per unit volume) as large as that in the comparative example 2. Further, the embodiment 1 was greatly improved in dark current. Further, when the radio-conductive material was formed by liquid deposition process (embodiment 1), the photocurrent was 1.3 times as large as that when the radio-conductive material was formed by melt deposition process (comparative example 1). Further, handling properties were improved and stability of the radio-conductive material manufactured was highly improved.

As can be understood from the description above, in the radio-conductive film in accordance with the first to third aspects of the present invention, the inorganic material is highly uniformly dispersed in the organic material as compared with the conventional radio-conductive layer, and accordingly, the radio-conductive film is free from agglomerates of the inorganic particles, whereby the film can be better in radio-conductive properties, is less apt to cause electric charge trapping, and can be small in dark current which flows while the film is not being exposed to radiations.

The radio-conductive material and the solid sensor in accordance with the fourth and fifth aspects of the present invention will be described in more detail, hereinbelow.

The radio-conductive material in accordance with the fourth aspect of the present invention is represented by the following formula (I), $$BiI_3/x.MX/y.nylon \qquad (I),$$

wherein M represents at least one alkali metal selected from the group consisting of Li, Na, K, Rb and Cs, X represents at least one halogen selected from the group consisting of F, Cl, Br and I, and x and y respectively represent the ratios by weight of MX and nylon to $Bi_3$, x being $0<x<1$, and y being $0<y<4$. It is preferred that MX be potassium fluoride.

It is preferred that the nylon be alcohol-soluble. As described above, the alcohol-soluble nylon is a nylon which is solid at normal temperatures and is soluble in alcoholic solvent. For example, the alcohol-soluble nylon may be copolymer nylon obtained by copolymerizing various dibasic acids and diamines or nylon obtained by introducing an N-alkoxymethyl group into a polyamide binding of nylon.

The copolymer nylon is obtained by copolymerizing two or more dibasic acids and/or two or more diamines. As the diamine, hexamethylenediamine, heptamethylenediamine, p-diaminomethylcyclohexane, bis-(p-aminocyclohexyl) methane, m-xylenediamine, 1,4-bis(3-aminopropoxy)cyclohexane, piperazine, isophoronediamine and the like may be used. As the dibasic acid, adipic acid, sebacic acid, azelaic acid, dodecanoic acid, undecanoic acid, dimmer acid, phthalic acid, isophthalic acid, terephthalic acid, sodium 5-sulfoisophthalate, and the like may be used. Further the alcohol-soluble nylon may be produced from aminocarboxylic acids such as 11-aminoundecanoic acid, 12-aminododecanoic acid, 4-aminomethylbenzoic acid, 4-aminomethylcyclohexanecarboxylic acid, 7-aminoenanthic acid, and 9-aminononanoic acid, and lactams such as ϵ-caprolactam, ω-laurolactam, α-pyrrolidone, and α-piperidone. The alcohol-soluble nylons obtained from these compounds include nylon 6/nylon 66, nylon 6/nylon 6–10, nylon 6/nylon 66/nylon 6–10, nylon 6/nylon 66/nylon 11, nylon 6/nylon 66/nylon 12, nylon 6/nylon 6–10/nylon 6–11, nylon 6/nylon 6–10/nylon 6–12, nylon 6/nylon 11/isophoronediamine, nylon 6/nylon 66/p-di(aminocyclohexyl)methane and the like. Among those, composite material of nylon 6 and nylon 66 is especially preferred.

The alcohol-soluble nylon may be obtained by introducing an N-alkoxymethyl group into a polyamide binding of nylon. For example, nylon obtained by alkoxymethylation of nylon 6 or nylon 66 may be used. Introduction of an N-alkoxymethyl group contributes to lowering the melting point, increasing flexibility and improving dissolution.

Such alcohol-soluble nylons are wide known and may be manufactured according to the process disclosed in, for instance, “Nylon Resin Handbook”, and “Journal of American Chemical Society” (71, 651, 1949).

It is preferred that when alcohol-soluble nylon is employed, the alkali halide represented by MX be also alcohol-soluble.

In formula (I), it is preferred that x be in the range of $0<x\leqq 0.2$ from the viewpoint of X-ray absorbance and y be in the range of $0.1<y\leqq 1$ from the viewpoint of maintenance of shape and X-ray absorbance.

When alcohol-soluble nylon is employed, the alcohol in which the alcohol-soluble nylon is dissolved may be methanol, ethanol, isopropyl alcohol, n-propyl alcohol, isobutyl alcohol, n-butyl alcohol and the like. In order to evaporate the alcohol after dissolving the nylon and the inorganic material in the alcohol to obtain high-viscosity composite material, methanol and ethanol are preferred. It is preferred that the alcohol be dehydrated, for instance, by a molecular sieve. Though depending upon the kinds of alcohol to be used, the alcohol-soluble nylon/bismuth iodide/alkali halide ratio of the mixture to be dissolved in the alcohol, and the like, it is preferred that the alcohol be used in an amount sufficient for the nylon to be dissolved in the alcohol and for the bismuth iodide to be satisfactorily dispersed in the alcohol.

When alcohol-soluble nylon is employed, the radio-conductive material in accordance with the fourth aspect of the present invention may be manufactured by the “liquid deposition process”, where the alcohol-soluble nylon and the bismuth iodide are dissolved in alcohol, then alkali halide is added to the mixture, and the alcohol is evaporated to obtain high-viscosity composite material.

When alcohol-insoluble nylon is employed, the radio-conductive material in accordance with the fourth aspect of the present invention may be manufactured by the so-called “melt deposition process” in which the nylon is melted on a substrate heated by a hot plate or the like, bismuth iodide is added to the molten nylon, the alkali halide is then added and the mixture is stirred by, for instance, a spatula.

The manufacture of the radio-conductive material in accordance with the fourth aspect of the present invention by the “liquid deposition process” will be described in detail with reference to FIG. 1 taking as example the case where the nylon is alcohol-soluble nylon (nylon 6/nylon 66 composite material) and the alkali halide is potassium fluoride (KF). Bismuth iodide ($BiI_3$) and nylon 6/nylon 66 composite material (in the ratio of 65–50/35–50% by weight) are introduced into alcohol in a beaker 101 and the mixture is heated to a predetermined temperature by a heating apparatus (e.g., a hot plate) 102 while stirring the mixture as shown in FIG. 1 so that the bismuth iodide and the nylon are satisfactorily dissolved in the alcohol. Though depending upon the kind of the alcohol, the predetermined temperature is preferably in the range of a room temperature (about 25° C.) to 60° C. Then KF is added. The ratio of $BiI_3$/KF/nylon 6/nylon 66 composite material/methanol is, for instance, 1 g:0.1 g:1 g:100 ml. Then the mixture is heated at 60° C. while stirring the mixture, thereby further evaporating the alcohol to obtain high-viscosity $BiI_3$/KF/nylon 6/nylon 66 composite material. Then the high-viscosity composite material is dropped onto a substrate 103 of aluminum, ITO or the like and is formed into a film by the use of a spatula or the like. Thereafter the substrate 103 bearing thereon the film of $BiI_3$/KF/nylon 6/nylon 66 composite material is left in methanol and is gradually dried. If desired other materials such as additives may be added for various purposes.

The radio-conductive material in accordance with the fourth aspect of the present invention can be employed in place of the radio-conductive material in accordance with the first aspect of the present invention to form the radio-conductive layer 2 in the solid sensor 10 shown in FIG. 2.

Films of X-ray-conductive material in accordance with the fourth aspect of the present invention (embodiments 2 to 9) were produced together with a film of X-ray-conductive material not in accordance with the fourth aspect of the present invention (comparative example 3) in the following manner.

EMBODIMENT 2

1 g of bismuth iodide, 1 g of nylon CM4000 (available from Toray: nylon 6/nylon 66 composite material) and 0.02 g of LiI were introduced into 100 ml of methanol which had been dehydrated by a molecular sieve, and the mixture was stirred at 60° C. so that $Bi_3$, the nylon and LiI were satisfactorily dissolved in the methanol. Then the mixture was heated at 60° C. while stirring the mixture, thereby further evaporating the methanol to obtain high-viscosity $BiI_3$/LiI/nylon CM4000 composite material. Then the high-viscosity composite material was dropped onto an aluminum substrate (at 0 to 50° C.) and was formed into a film by the use of a spatula at the room temperature. Thereafter the substrate bearing thereon the film of $BiI_3$/LiI/nylon CM 4000 composite material was left in methanol and gradually dried. The film obtained exhibited X-ray-conductivity and was 200 μm in thickness.

EMBODIMENT 3

An X-ray-conductive film 200 μm thick was obtained in the same manner as the embodiment 2 except that KI was employed in place of LiI.

EMBODIMENT 4

An X-ray-conductive film 200 μm thick was obtained in the same manner as the embodiment 3 except that KI was employed in 0.2 g.

EMBODIMENT 5

An X-ray-conductive film 200 μm thick was obtained in the same manner as the embodiment 3 except that nylon CM4000 was employed in 0.43 g ($BiI_3$/nylon CM400=70/30) and KI was employed in 0.14 g.

EMBODIMENT 6

An X-ray-conductive film 200 μm thick was obtained in the same manner as the embodiment 4 except that KF was employed in place of KI.

EMBODIMENT 7

An X-ray-conductive film 200 μm thick was obtained in the same manner as the embodiment 5 except that KF was employed in 0.05 g.

EMBODIMENT 8

An X-ray-conductive film 200 μm thick was obtained in the same manner as the embodiment 5 except that KCl was employed in place of KF.

EMBODIMENT 9

An X-ray-conductive film 200 μm thick was obtained in the same manner as the embodiment 5 except that NaI was employed in place of KF.

COMPARATIVE EXAMPLE 3

An X-ray-conductive film 200 μm thick was obtained in the same manner as the embodiment 2 except that no alkali halide was added.

Evaluation

The photocurrents upon exposure to an X-ray of the X-ray-conductive films of the embodiments 2 to 9 and the comparative example 3 were measured. The photocurrent was measured as a photocurrent per unit volume by sputtering gold in a size of 5 mm×5 mm×600 Å on the X-ray-conductive films and by the use of a D1 photoconductivity evaluation apparatus (X-ray: 80 kV-10~100 mR, detection: pico-ammeter) and a D6 photoconductivity evaluation apparatus (X-ray: 80, 120 kV-20 mR, detection: digital oscilloscope) The photocurrents were represented with the measured value for the comparative example 3 taken as 1. The result is shown in the following table 2.

TABLE 2

| | $BiI_3$ (g) | alkali halide/g | nylon (g) | photocurrent (relative value) |
|---|---|---|---|---|
| emb. 2 | 1.0 | LiI/0.02 | 1.0 | 2.87 |
| emb. 3 | 1.0 | KI/0.02 | 1.0 | 2.62 |
| emb. 4 | 1.0 | KI/0.2 | 1.0 | 4.50 |
| emb. 5 | 1.0 | KI/0.14 | 0.43 | 4.35 |
| emb. 6 | 1.0 | KF/0.14 | 0.43 | 8.01 |
| emb. 7 | 1.0 | KF/0.05 | 0.43 | 1.38 |
| emb. 8 | 1.0 | KCl/0.14 | 0.43 | 3.85 |
| emb. 9 | 1.0 | NaI/0.14 | 0.43 | 4.37 |
| comp. EX. 3 | 1.0 | — | 1.0 | 1.00 |

As can be understood from table 2, when alkali halide was added, the photocurrent was 1.4 to 8 times as large as that when no alkali halide was added.

As can be understood from the description above, in the radio-conductive film in accordance with the fourth aspect of the present invention, the radiation absorbing power of the radio-conductive material can be increased.

The methods of manufacturing a radio-conductive film in accordance with the sixth and seventh aspects of the present invention will be described in more detail, hereinbelow.

In accordance with the sixth and seventh aspects of the present invention, the radio-conductive film is manufactured by pressing the inorganic/organic composite radio-conductive material or heating an inorganic/organic composite radio-conductive material film.

The inorganic material having radiation absorbing power may be $V_B$–$VI_B$, $V_B$–$VII_B$, $II_B$–$VI_B$, $II_B$–$V_B$, $III_B$–$V_B$, $III_B$-$VI_B$, $I_B$–$VI_B$ or $IV_B$–$VII_B$ inorganic material. For example, the inorganic material may be $Bi_2S_3$, $Bi_2Se_3$, $BiI_3$, $BiBr_3$, CdS, CdSe, CdTe, HgS, $Cd_2P_3$, InAs, InP, $In_2S_3$, $In_2Se_3$, $Ag_2S$, $PbI_2$ or $PbI_4^{2-}$. Among those, $BiI_3$ (bismuth iodide) is especially preferred.

As the organic material, nylon 11, PVK (N-polyvinyl carbazole) or PMMA (polymethyl methacrylate) can be used. When $BiI_3$ is employed as the inorganic material, it is preferred that the organic material be nylon in that nylon has an amide binding and is apt to interact with $BiI_3$ as a Shiff base. Though the nylon may be soluble to alcohol, insoluble to alcohol or hard to dissolve in alcohol, the alcohol-soluble nylon is preferred from the viewpoint of easiness in preparation of radio-conductive material and dispersion of $BiI_3$.

When alcohol-soluble nylon employed, the radio-conductive material may manufactured by the "liquid deposition", process where the alcohol-soluble nylon and the inorganic material are dissolved in alcohol, and the alcohol is evaporated to obtain high-viscosity composite material. The high-viscosity composite material may be spread in a film on a substrate.

When alcohol-insoluble nylon is employed, the radio-conductive material may be manufactured by the so-called "melt deposition process" in which the nylon is melted on a substrate heated by a hot plate or the like, the inorganic material is added to the molten nylon, and the mixture is stirred by, for instance, a spatula.

As the substrate, those which are not broken or deformed by pressing and/or heating, can function as an electrode, are good in heat conductivity, are good in flatness and are well bonded to the radio-conductive material are preferred, and for instance, an aluminum plate and an ITO plate are preferred.

Figure 9:
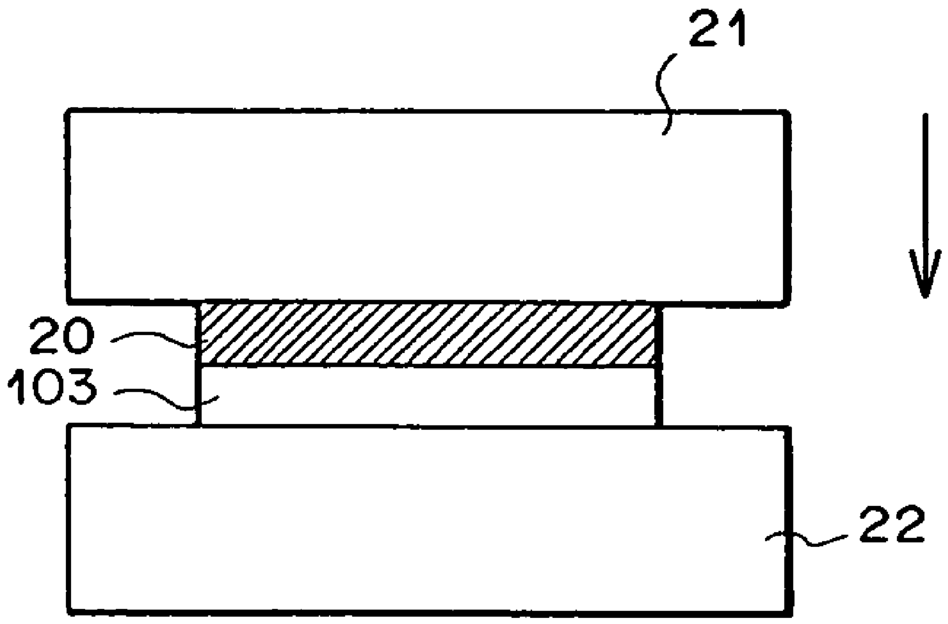
FIG. 9 is a view showing a pressing/heating apparatus for carrying out the method in accordance with the sixth aspect of the present invention.

The radio-conductive material may be pressed by the use of any apparatus so long as it can uniformly press the material. However it is preferred that the apparatus be provided with a temperature controller. For example, a pressing apparatus shown in FIG. 9 is preferable. The substrate 103 with radio-conductive material layer 20 is placed between upper and lower heating plates 21 and 22 and the upper heating plate 21 is pressed toward the lower heating plate 22 at a uniform pressure as shown by the arrow with the four corners of the substrate 103 kept fixed. The upper heating plate 21 may be formed, for instance, of carbon steel SK3 and the lower heating plate 22 may be formed, for instance, of rolled steel for general structural material SS41. The higher the pressure to be applied to the radio-conductive material layer 20 is, the more the voids are removed. However, it is preferred that the pressure be not higher than 50 kg/cm$^2$ so that the substrate 103 is not broken or deformed. It is preferred that the substrate 103 be heated during pressing to a temperature, which is preferably in the range of 50 to 200° C., and more preferably in the range of 120 to 190° C.

When the radio-conductive material is pressed with a member, having a smooth surface which does not adhere to the radio-conductive material, as pre-treatment, a radio-conductive film which is better in flatness and uniformity can be obtained.

When a radio-conductive material film is heated to form a radio-conductive film, the radio-conductive material film is held at 50 to 200° C. (preferably 120 to 190° C.) for two or three hours in a constant temperature room. The radio-conductive material film may be heated under a normal pressure or a negative pressure (may be very close to vacuum).

The radio-conductive film manufactured in accordance with the sixth or seventh aspect of the present invention may be used as the radio-conductive layer 2 of the solid sensor shown in FIG. 2.

X-ray-conductive films were manufactured in accordance with methods of the sixth aspect or the seventh aspect of the present invention (embodiments 10 to 19) and in accordance with a method not in accordance with the sixth or seventh aspect of the present invention (a comparative example 4) in the following manner.

EMBODIMENT 10

1 g of bismuth iodide and 1 g of nylon CM4000 (available from Toray: nylon 6/nylon 66 composite material) were introduced into 100 ml of methanol which had been dehydrated by a molecular sieve, and the mixture was stirred at 60° C. so that the bismuth iodide and the nylon were satisfactorily dissolved in the methanol. Then the mixture was heated at 60° C. while stirring the mixture, thereby further evaporating the methanol to obtain high-viscosity bismuth iodide/nylon CM4000 composite material. Then the high-viscosity composite material was dropped onto an aluminum substrate (at 0 to 50° C.) and was formed into a film by the use of a spatula at the room temperature. Thereafter the substrate bearing thereon the film of bismuth iodide/nylon CM 4000 composite material was left in methanol and gradually dried, whereby a radio-conductive material film was obtained. The radio-conductive material film was compressed under a pressure of 15 kg/cm$^2$ at 70° C. by the apparatus shown in FIG. 9. The radio-conductive film obtained exhibited X-ray-conductivity and was 180 $\mu$m in thickness.

EMBODIMENT 11

An X-ray-conductive film 180 $\mu$m thick was obtained in the same manner as the embodiment 10 except that the pressure applied to the radio-conductive material film was changed 32 kg/cm$^2$.

EMBODIMENT 12

An X-ray-conductive film 170 $\mu$m thick was obtained in the same manner as the embodiment 10 except that the pressure applied to the radio-conductive material film was changed 70 kg/cm$^2$.

EMBODIMENT 13

An X-ray-conductive film 170 $\mu$m thick was obtained in the same manner as the embodiment 10 except that radio-conductive material film was compressed at 110° C.

EMBODIMENT 14

An X-ray-conductive film 180 $\mu$m thick was obtained in the same manner as the embodiment 13 except that the pressure applied to the radio-conductive material film was changed 25 kg/cm$^2$.

EMBODIMENT 15

An X-ray-conductive film 170 $\mu$m thick was obtained in the same manner as the embodiment 13 except that the pressure applied to the radio-conductive material film was changed 55 kg/cm$^2$.

EMBODIMENT 16

The radio-conductive material film obtained by the embodiment 10 was held at 50° C. for three hours in a constant temperature room and then cooled to the room temperature, whereby an X-ray-conductive film 180 $\mu$m thick was obtained.

EMBODIMENT 17

An X-ray-conductive film 180 $\mu$m thick was obtained in the same manner as the embodiment 16 except that the radio-conductive material film was held at 100° C.

EMBODIMENT 18

An X-ray-conductive film 180 $\mu$m thick was obtained in the same manner as the embodiment 16 except that the radio-conductive material film was held at 150° C.

EMBODIMENT 19

An X-ray-conductive film 180 $\mu$m thick was obtained in the same manner as the embodiment 16 except that the radio-conductive material film was held at 200° C.

COMPARATIVE EXAMPLE 4

A radio-conductive film was obtained from the radio-conductive material film obtained by the embodiment 10 without pressing or heating. The radio-conductive film obtained exhibited X-ray-conductivity and was 200 $\mu$m in thickness.

Evaluation

Figure 10:
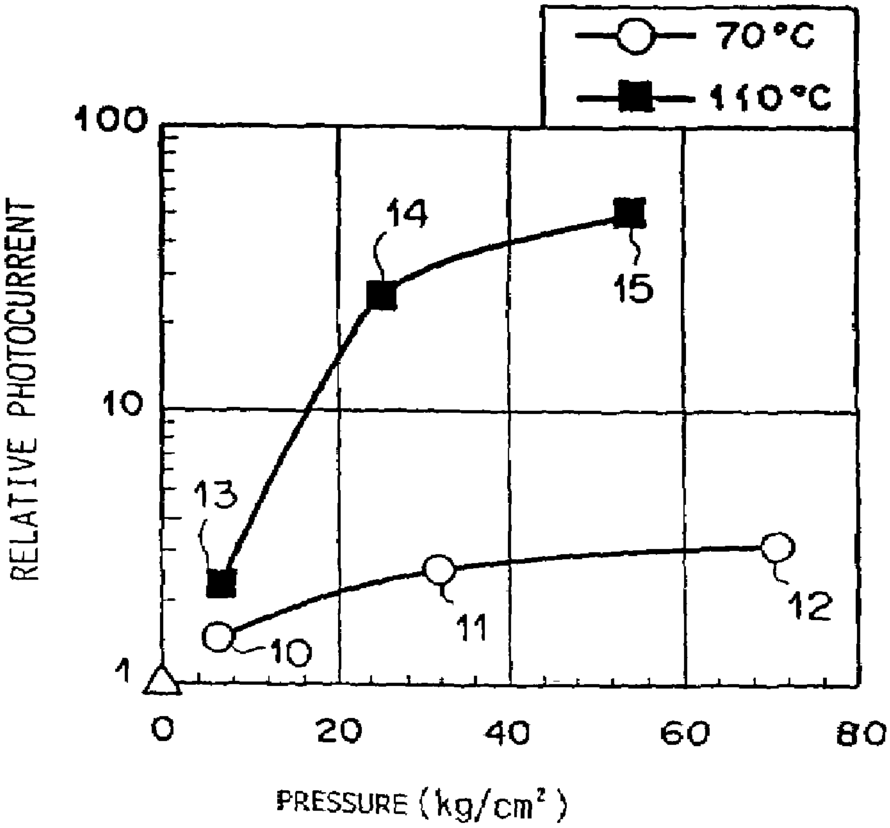
FIG. 10 is a graph showing the relation between the pressure and the temperature applied to the radio-conductive material film and the relative values of the photocurrents of the radio-conductive film obtained.
Figure 11:
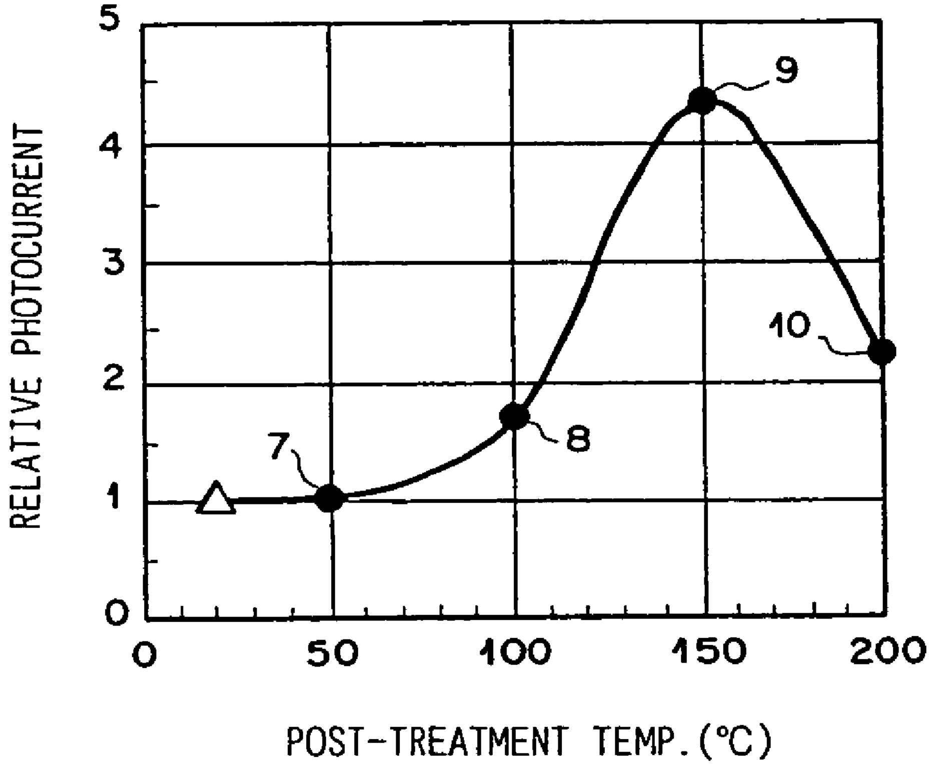
FIG. 11 is a graph showing the relation between the temperature applied to the radio-conductive material film and the relative values of the photocurrents of the radio-conductive film obtained.

The photocurrents upon exposure to an X-ray of the X-ray-conductive films of the embodiments 10 to 19 and the comparative example 4 were measured. The photocurrent was measured as a photocurrent per unit volume by sputtering gold in a size of 5 mm×5 mm×600 Å on the X-ray-conductive films and by the use of a D1 photoconductivity evaluation apparatus (X-ray: 80 kV-10~100 mR, detection: pico-ammeter) and a D6 photoconductivity evaluation apparatus (X-ray: 80, 120 kV-20 mR, detection: digital oscilloscope). The photocurrents were represented with the measured value for the comparative example 4 taken as 1. The result is shown in FIGS. 10 and 11. FIG. 10 is a graph showing the relation between the pressure and the temperature applied to the radio-conductive material film and the relative values of the photocurrents of the radio-conductive film obtained, and FIG. 11 is a graph showing the relation between the temperature applied to the radio-conductive material film and the relative values of the photocurrents of the radio-conductive film obtained. In FIGS. 10 and 11, Δ shows the value for the comparative example 4 and figures on the lines denote the numbers of embodiments.

As can be understood from FIG. 10, when the radio-conductive material film was pressed, the photocurrent was increased by two to fifty times as compared with when the film was not pressed or heated irrespective of whether the film was heated to 70° C. or 110° C. Further, as can be understood from FIG. 5, by only heating the radio-conductive material film, the photocurrent can be increased by 4.3 times at most.

In accordance with the eighth aspect of the present invention, the first electrode 1 of the solid sensor 10 shown in FIG. 2 is formed of indium. The indium electrode 2 may be formed on the recording radio-conductive layer 2 by known methods such as vacuum deposition, sputtering, plasma CVD, optical CVD and the like.

Solid sensors in accordance with the eighth aspect of the present invention (embodiment 20) and not in accordance with the eighth aspect of the present invention (a comparative example 5) were prepared in the following manner.

EMBODIMENT 20

Figure 12:
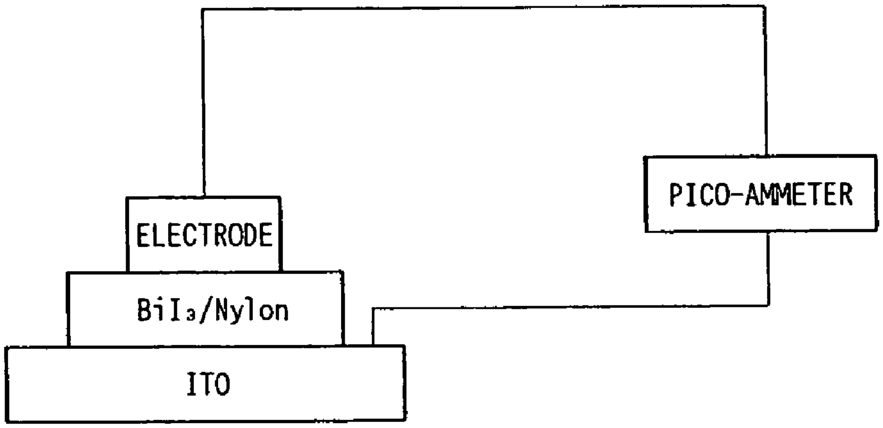
FIG. 12 is a view schematically showing a photoconductivity evaluation apparatus.

1 g of bismuth iodide and 1 g of nylon CM4000 (available from Toray: nylon 6/nylon 66 composite material) were introduced into 100 ml of methanol which had been dehydrated by a molecular sieve, and the mixture was stirred at 60° C. so that the bismuth iodide and the nylon were satisfactorily dissolved in the methanol. Then the mixture was heated at 60° C. while stirring the mixture, thereby further evaporating the methanol to obtain high-viscosity bismuth iodide/nylon CM4000 composite material. Then the high-viscosity composite material was dropped onto an aluminum substrate (at 0 to 50° C.) and was formed into a film by the use of a spatula at the room temperature. Thereafter the substrate bearing thereon the film of bismuth iodide/nylon CM 4000 composite material was left in methanol and gradually dried. The film obtained exhibited X-ray-conductivity and was 200 μm in thickness. Indium was sputtered on the X-ray-conductive film in a size of 5 mm×5 mm×600 Å. Then the photocurrent was measured by the use of an X-ray-conductivity evaluation apparatus shown in FIG. 12.

COMPARATIVE EXAMPLE 5

The photocurrent was measured in the same manner as the embodiment 20 except that gold was sputtered on the X-ray-conductive film in a size of 5 mm×5 mm×600 Å in place of indium.

Figure 13:
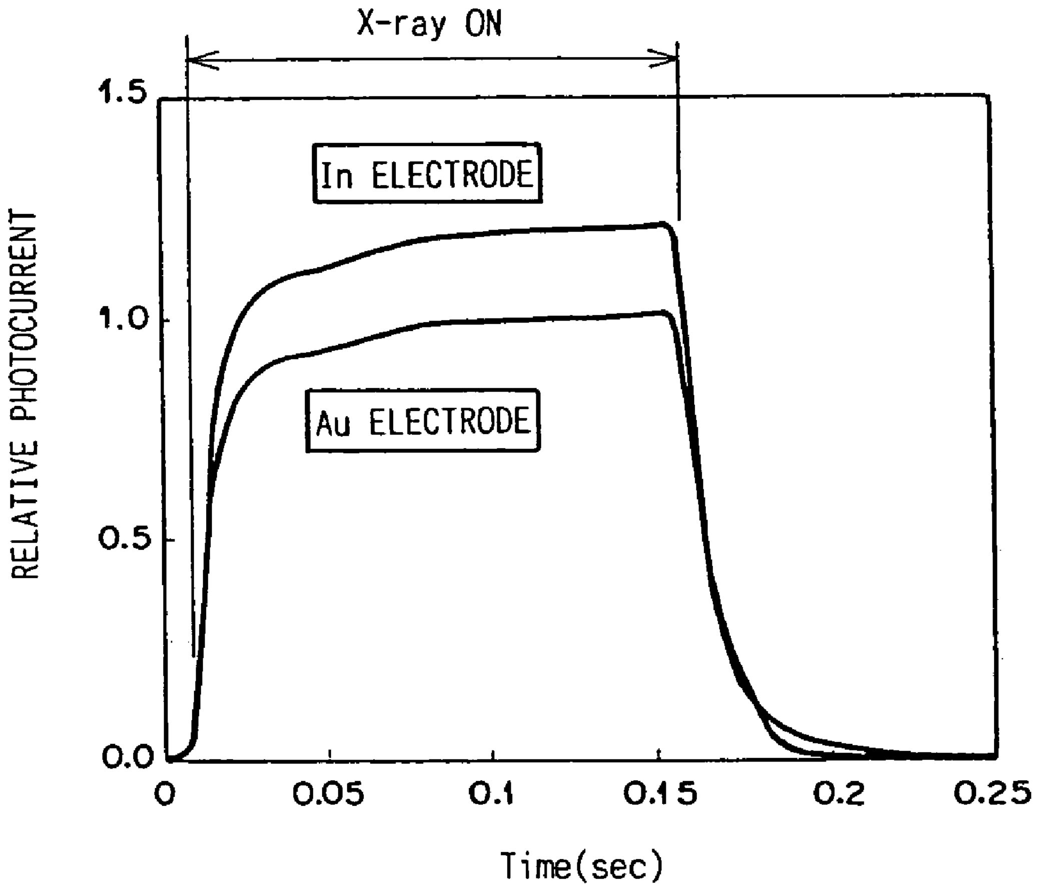
FIG. 13 is a graph showing the relation between the relative photocurrent and the X-ray irradiating time.

FIG. 13 shows the relation between the relative photocurrent and the X-ray irradiating time for embodiment 20 and comparative example 5. As can be understood from FIG. 13, when the indium electrode was used, the photocurrent increased by about 1.2 times as compared with when the gold electrode was used. Further, when the indium electrode was used, the stray current was reduced.

As can be understood from the description above, by the use of an electrode of indium which is stable at normal temperatures, is superior in processing characteristics, and can be almost freely deformed and can be in close contact with the radio-conductive layer formed of inorganic/organic composite material (having microscopic unevenness) without any gap formed therebetween, whereby electric charges generated in the radio-conductive layer upon exposure to radiations can be immediately moved to the electrode without generating a stray current and the radio-conductivity of the solid sensor can be improved.

What is claimed is:

1. A method of manufacturing a radio-conductive film of an inorganic/organic composite radio-conductive material comprising the step of pressing the inorganic/organic composite radio-conductive material, wherein the radio-conductive material is pressed in a state where the radio-conductive material is formed on a substrate, and the radio-conductive material is pressed at a pressure not higher than 50 kg/cm$^2$.

2. A method as defined in claim 1 in which the inorganic/organic composite radio-conductive material is pressed at an elevated temperature.

3. A method as defined in claim 2 in which the elevated temperature is in the range of 50° C. to 200° C.

4. A method as defined in claim 1 in which the inorganic/organic composite radio-conductive material is $BiI_3$/nylon.

5. A method as defined in claim 1, wherein said process further comprises the step of heating a film of inorganic/organic composite radio-conductive material, and wherein a film of inorganic/organic composite radio-conductive material is pressed during pressing.

6. A method as defined in claim 5 in which the elevated temperature is in the range of 50° C. to 200° C.

7. A method as defined in claim 5 in which the inorganic/organic composite radio-conductive material is $BiI_3$/nylon.

* * * * *